(12) United States Patent
Chen et al.

(10) Patent No.: US 10,272,182 B2
(45) Date of Patent: Apr. 30, 2019

(54) COPOLYMER MEMBRANE FOR HIGH-DOSE CHEMOTHERAPY DELIVERY DURING TRANSARTERIAL CHEMOEMBOLIZATION

(71) Applicant: THE REGENTS OF THE UNIVERSITY OF CALIFORNIA, Oakland, CA (US)

(72) Inventors: Xi Chelsea Chen, Berkeley, CA (US); Jeffrey Yang, San Francisco, CA (US); Albert Chin, Palo Alto, CA (US); Anand Patel, San Francisco, CA (US); Steven Hetts, San Francisco, CA (US); Nitash Balsara, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 248 days.

(21) Appl. No.: 14/880,925

(22) Filed: Oct. 12, 2015

(65) Prior Publication Data

US 2016/0101218 A1    Apr. 14, 2016

Related U.S. Application Data

(60) Provisional application No. 62/062,629, filed on Oct. 10, 2014.

(51) Int. Cl.

| | |
|---|---|
| *A61L 29/04* | (2006.01) |
| *A61M 25/00* | (2006.01) |
| *B01D 71/66* | (2006.01) |
| *B01D 71/80* | (2006.01) |
| *B01D 69/02* | (2006.01) |
| *B01D 71/26* | (2006.01) |
| *A61L 29/16* | (2006.01) |
| *A61M 1/36* | (2006.01) |

(52) U.S. Cl.
CPC ............ *A61L 29/041* (2013.01); *B01D 69/02* (2013.01); *B01D 71/80* (2013.01); *A61M 1/3615* (2014.02); *A61M 2207/00* (2013.01); *B01D 71/26* (2013.01); *B01D 71/66* (2013.01); *B01D 2325/02* (2013.01); *B01D 2325/04* (2013.01); *B01D 2325/20* (2013.01)

(58) Field of Classification Search
CPC ................. B01D 69/02; B01D 71/82
See application file for complete search history.

(56) References Cited

U.S. PATENT DOCUMENTS

| | | | | |
|---|---|---|---|---|
| 6,306,419 | B1 * | 10/2001 | Vachon | A61K 9/7023 424/422 |
| 2011/0053043 | A1 * | 3/2011 | Balsara | B01D 69/02 429/493 |

FOREIGN PATENT DOCUMENTS

| | | | | |
|---|---|---|---|---|
| WO | WO-2012129411 A1 * | 9/2012 | ......... | H01M 2/1653 |
| WO | WO 2014100201 A1 * | 6/2014 | ............ | A61F 2/013 |

OTHER PUBLICATIONS

Patel et al., Journal of Vascular and Interventional Radiology, 24: S124 (2013).*
Patel et al., ASME, J. Med. Devices, 8: 041008-1-041008.8, pub. online Aug. 19, 2014.*
Chen et al., NanoLetters, 14:4058-4064, pub. online May 22, 2014.*
Chen et al. (Macromolecules, 48: 5648-5655 (2015, published online Aug. 10, 2015). (Year: 2015).*

* cited by examiner

*Primary Examiner* — Anna R Falkowitz
(74) *Attorney, Agent, or Firm* — Womble Bond Dickinson (US) LLP (57) ABSTRACT

Described herein is a porous copolymer membrane composed of poly(styrene sulfonate)-block-polyethylene-block-poly(styrenesulfonate) for use in the absorption of doxorubicin, and a chemofiltration catheter incorporating the membrane for use in transarterial chemoembolization.

7 Claims, 10 Drawing Sheets

COPOLYMER MEMBRANE FOR HIGH-DOSE CHEMOTHERAPY DELIVERY DURING TRANSARTERIAL CHEMOEMBOLIZATION

CROSS-REFERENCE TO RELATED APPLICATION

This application claims the benefit of priority to U.S. Provisional Patent Application No. 62/062,629, filed Oct. 10, 2014, which is hereby incorporated by reference herein in its entirety.

STATEMENT OF GOVERNMENT RIGHTS

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

TECHNICAL FIELD

The embodiments of the present disclosure relates to the field of cancer therapy, and more particularly to materials and devices for use in transarterial chemoembolization.

BACKGROUND

Hepatocellular carcinoma (HCC) is the fifth most common cancer in the world, with approximately 500,000 new cases per year worldwide, and is the third leading cause of cancer deaths worldwide. The treatment of HCC includes surgical resection, liver transplantation, and palliative care, depending on the advancement of the disease. For patients with unresectable HCC, transarterial chemoembolization (TACE) has clinically been proven to be superior to conservative palliative treatment.

TACE therapy is usually performed by an interventional radiologist (IR). Generally, a microcatheter is positioned through a guidewire into the main artery that feeds the tumor. An emulsion of chemotherapy agent or mixture of agents (commonly doxorubicin and cisplatin) suspended in lipiodol (an oily contrast medium that is preferably retained by tumor tissue) is injected intra-arterially into the hepatic arteries that directly feed the tumor. This is followed by blocking the feeding arteries with an embolic agent. The combination of the chemotherapy and arterial occlusion leads to increased drug residency time with the tumor. Furthermore, by concentrating the drug within the tumor tissue, one might expect reduced systemic exposure. However, even with TACE, up to 50% of the administered drug enters systemic circulation.

Thus, in the treatment of HCC, there is a demand for new chemotherapy delivery systems to improve drug dose local to the tumor and to minimize systemic exposure.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION

Described herein in certain embodiments is a highly porous block copolymer electrolyte membrane that can be utilized as a filter for rapid binding of therapeutic agents used in chemotherapy, such as doxorubicin (dox). The membrane may be deployed in the draining vein of the tumor (i.e. hepatic vein, renal vein, or inferior vena cava) by a catheter and used in conjunction with transarterial chemoembolization (TACE) to increase the local dose to the tumor tissue and bind the therapeutic agent before it enters systemic circulation. In certain embodiments, the active drug binding component of the membrane is sulfonated polystyrene. Endovascular catheter-based chemofiltration (CF) devices were developed and tested in vitro. A large animal model for further in vivo testing has also been established with data supporting rapid high-capacity dox binding in vivo from blood.

Advantages of some embodiments may include (1) high binding capacity, (2) fast binding kinetics, 3) reduced thrombogenicity, and (4) applicability to a large market. The embodiments described herein can serve as a platform technology for a new paradigm in drug therapy, enabling well-established, low-cost drugs to be used at higher doses, leading to lower toxicity and improved clinical outcomes. In clinical use for the treatment of hepatocellular carcinoma (HCC), for example, a CF device could be used in patients with secondary liver tumors undergoing intra-arterial chemotherapy (IAC), such as those patients with liver metastases from a number of malignancies. The CF device could also be adapted to treat nearly any solid organ tumor (kidney cancer, lung cancer, breast cancer, etc.), and could be adapted for treatment by therapeutic agents other than dox. Although a particularly useful application of disclosed embodiments is in locoregional cancer chemotherapy, paired intraarterial infusion and venous filtration can potentially be used for any drug that has its site of therapeutic action in one location and its site of dose-limiting toxicity in another location.

Figure 1:
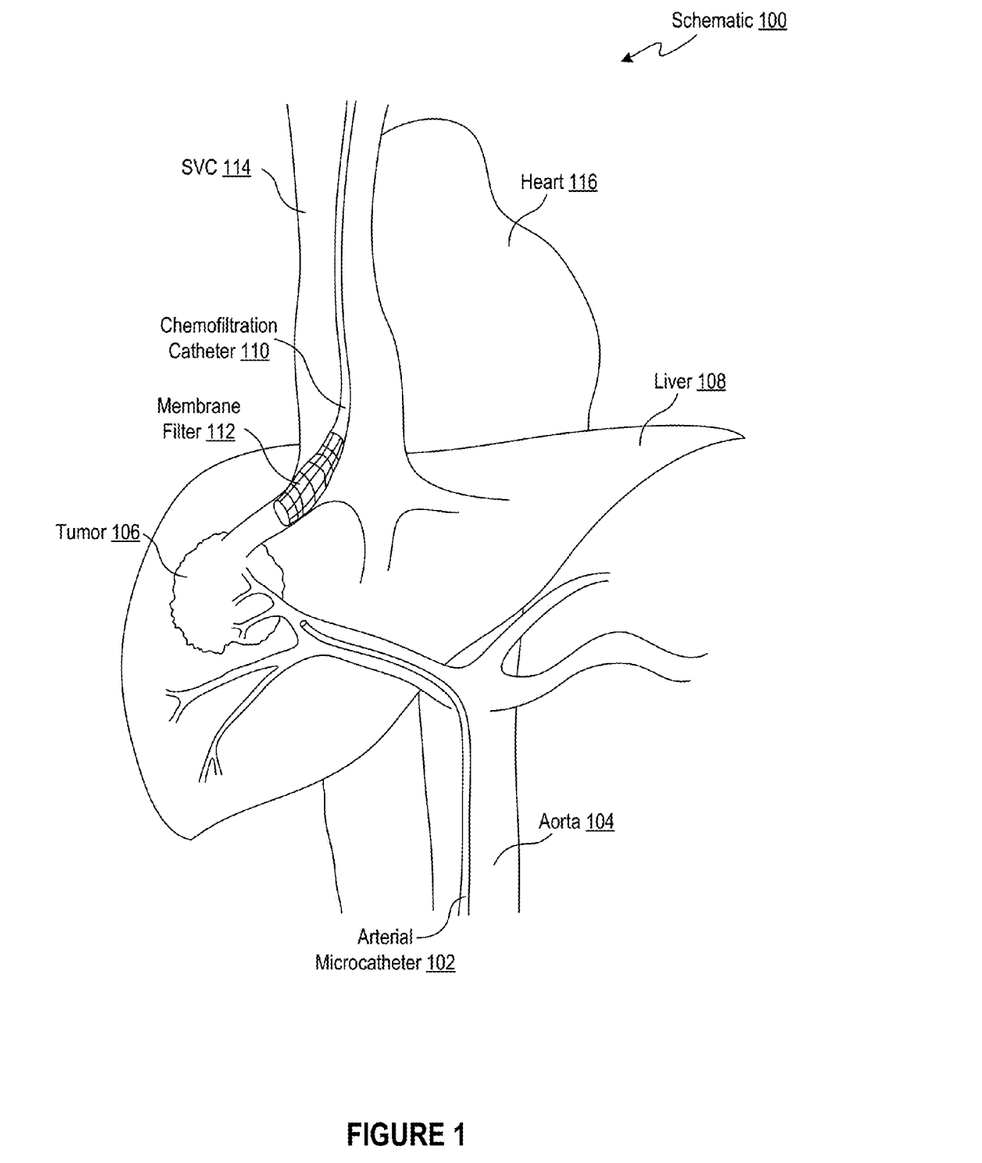
FIG. 1 is a schematic illustrating intra-arterial chemotherapy delivery procedure.

FIG. 1 is a schematic 100 illustrating an intra-arterial chemotherapy delivery procedure, which may be performed in accordance with an embodiment of the disclosure. From a percutaneous femoral approach, an arterial microcatheter 102 is guided through the aorta 104 into the arteries feeding a tumor 106 in the liver 108 to directly infuse the tumor 106 with a therapeutic agent (e.g., dox). From a percutaneous jugular approach, a CF catheter 110 is guided through the superior vena cava (SVC) 114 of the heart 116 and deployed in the veins draining the liver 108. The CF catheter 110 filters the therapeutic agent using a membrane filter 112 in some embodiments or a resin-based filter in other embodiments.

Figure 2:
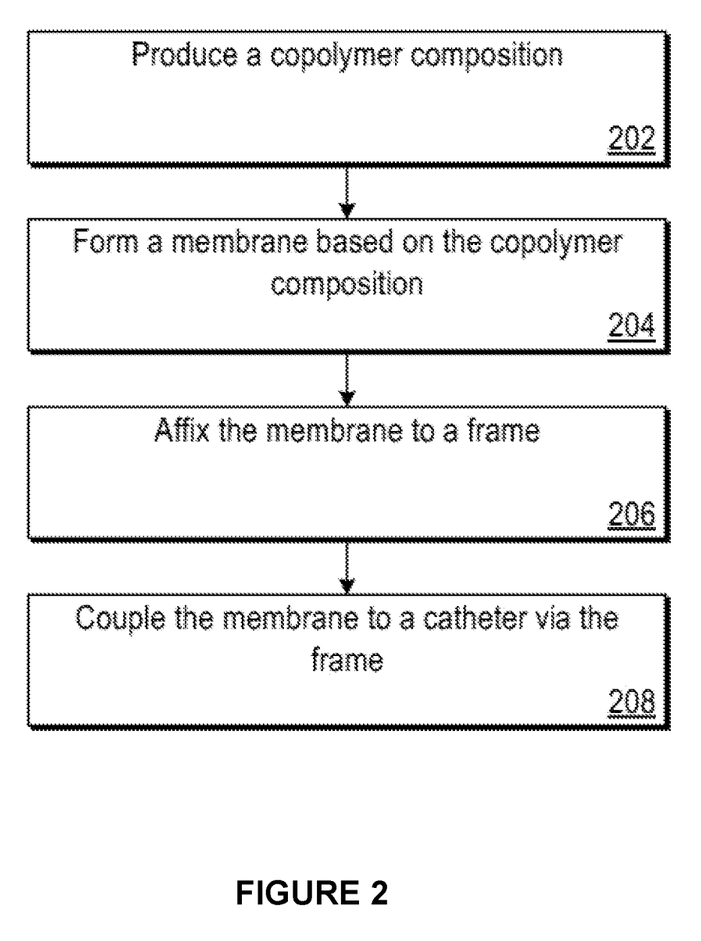
FIG. 2 is a flow diagram illustrating a method for preparing a catheter device in accordance with an embodiment of the present disclosure.

FIG. 2 is a flow diagram illustrating a method for preparing a catheter device in accordance with an embodiment of the present disclosure. At block 202, a copolymer composition (e.g., a triblock copolymer composition) is produced or provided. In certain embodiments, the copolymer composition comprises a sulfonated triblock copolymer, such as sulfonated polystyrene-block-polyethylene-block-polystyrene (poly(styrene sulfonate)-block-polyethylene-block-poly(styrene sulfonate)). In certain embodiments, a first molecular weight of each sulfonated polystyrene block ranges from 14 to 24 kg/mol, and a second molecular weight of the polyethylene block ranges from 32 to 42 kg/mol. In certain embodiments, producing the copolymer composition comprises first producing an initial triblock copolymer composition comprising polystyrene-block-polyethylene-block-polystyrene, followed by sulfonating the initial copolymer composition to produce a sulfonated triblock copolymer composition. In certain embodiments, the membrane comprises a copolymer composition selected from sulfonated polystyrene-block-polyethylene-block-polystyrene triblock copolymer, sulfonated poly(styrene-block-ethylene) diblock copolymer, sulfonated poly(styrene-block-ethylene/butylene) diblock copolymer, sulfonated poly(styrene-block-ethylene-block-styrene) triblock copolymer, sulfonated poly(ethylene-block-styrene-block-ethylene) triblock copolymer, sulfonated poly(styrene-block-ethylene/butylene-block-styrene) triblock copolymer, sulfonated poly(ethylene-block-styrene-block-ethylene) triblock copolymer, sulfonated poly(ethylene/butylene-block-styrene-block-ethylene/butylene) triblock copolymer, or combinations thereof. In certain embodiments, a sulfonation level of the copolymer composition, defined as a ratio of moles of sulfonated styrene monomer to total moles of styrene monomer, ranges from 15 to 80%, from 25 to 70%, from 35 to 60%, or from 40 to 50%.

At block 204, a membrane is formed, for example, by casting the copolymer composition (e.g., using a doctor blade), followed by a drying step in certain embodiments (e.g., heating at 60 to 120° C. for 18 to 36 hours). Other methods may be utilized to form the membrane, including, for example, spin coating, spraying, etc. In certain embodiments, a thickness of the membrane ranges from 10 to 100 micrometers, from 20 to 80 micrometers, or from 30 to 50 micrometers. Other suitable thicknesses may also be used.

In certain embodiments, an average pore volume fraction of the membrane ranges from 0 to 60%, from 10 to 60%, from 20 to 60%, from 30 to 60%, from 40 to 60%, from 0 to 50%, from 10 to 50%, from 20 to 50%, from 30 to 50%, from 10 to 40%, from 20 to 40%, or from 30 to 50%. As used herein, porosity of a membrane (or pore volume fraction), $\phi_v$, is defined as volume fraction of a component (such as polystyrene homopolymer) that was initially formed with the membrane and selectively dissolved out of the membrane. In certain embodiments, an average pore diameter of the membrane ranges from 2 nanometers to 3 micrometers, from 2 nanometers to 2 micrometers, from 2 nanometers to 1 micrometer, from 2 to 20 nanometers, from 5 to 20 nanometers, from 10 to 15 nanometers, from 20 nanometers to 3 micrometers, from 20 nanometers to 2 micrometers, from 20 nanometers to 1 micrometer, from 0.5 to 3 micrometers, from 0.5 to 2 micrometers, from 0.5 to 1 micrometers, from 1 to 3 micrometers, from 1 to micrometers, or from 2 to 3 micrometers.

At block 206, the membrane is affixed the membrane to a frame, such as a frame that is expandable to switch between a collapsed state and a deployed state. In certain embodiments, the frame comprises nitinol, stainless steel, titanium, other suitable biocompatible materials, or combinations thereof. In certain embodiments, the frame comprises a series of interconnected struts, and the membrane may be affixed to the struts by stitching.

At block 208, the membrane is coupled to a catheter via the frame. In certain embodiments, the catheter comprises a tubular housing. The frame may be disposed at a proximal end of the tubular housing, and may be incorporated into the tubular housing such that the frame is in the collapsed state when it is inside of the tubular housing, and is in the deployed state when the frame is forced out of the tubular housing at the proximal end. In such embodiments, the membrane is contained within the tubular housing when the frame is in the collapsed state, and the membrane is outside of the tubular housing and extends radially from the proximal end when the frame is in the deployed state. In other embodiments, the frame is incorporated onto an outside surface of the tubular housing, and is switchable between the collapsed and deployed states. In such embodiments, the membrane is collapsed along the exterior surface of the tubular housing when the frame is in the collapsed state, and extends radially from the tubular housing when the frame is in the deployed state.

ILLUSTRATIVE EXAMPLES

The following examples are set forth to assist in understanding the disclosed embodiments and should not be construed as specifically limiting the embodiments described and claimed herein. Such variations of the embodiments, including the substitution of all equivalents now known or later developed, which would be within the purview of those skilled in the art, and changes in formulation or minor changes in experimental design, are to be considered to fall within the scope of the embodiments described herein.

Copolymer Synthesis

Certain embodiments of the present disclosure are directed to copolymer compositions and the preparation thereof. An exemplary protocol for preparing a polystyrene-block-polyethylene-block-polystyrene (SES) copolymer composition, according to one embodiment, is now described.

Polystyrene (PS) homopolymer was synthesized by anionic polymerization using sec-butyl lithium as the initiator. The PS homopolymer was purified by precipitation in methanol, subsequently redissolved in benzene. Precipitation was repeated two additional times, followed by filtration through a 0.2 µm filter and lyophilization (Millrock LD85).

Copolymer polystyrene-block-polybutadiene-block-polystyrene (SBS) was synthesized by sequential anionic polymerization of styrene and butadiene, using sec-butyl lithium as the initiator, followed by the coupling of polystyrene-block-polybutadiene using dibromoethane to yield a symmetric polystyrene-block-polybutadiene-block-polystyrene triblock copolymer. The use of a nonpolar solvent (cyclohexane) resulted in approximately 93% 1,4-addition of the butadiene monomers. SBS was hydrogenated using p-toluenesulfonyl hydrazide in the presence of equimolar tri-n-propylamine to yield SES. SES copolymers were purified by precipitation into hydrochloric acid/methanol mixtures. The SES copolymers were then redissolved in o-xylene at 100° C. and precipitated into hydrochloric acid/methanol mixture two times, washed in a separatory funnel with excess deionized water three times, and redissolved in o-xylene at 100° C. and precipitated in pure methanol three times. The SES copolymers were then dried under vacuum at 80° C. for 10 days.

The molecular weights of PS and polybutadiene (PB) blocks of the SBS copolymer were obtained by extracting an aliquot of the reaction mixture during synthesis and performing the measurement using a Viscotek GPC Max VE-2001 gel permeation chromatographer equipped with a TDA 302 triple-detector system, which was calibrated using PS standards with tetrahydrofuran (THF) as the eluent. The volume fractions PS and PB of the SBS copolymer and the ratio of 1,4-addition over 1,2-addition in the PB blocks of the copolymer were determined using $^1$H nuclear magnetic resonance (NMR) spectroscopy (CDCl$_3$, 25° C.). High temperature NMR (toluene-d$_8$, 90° C.) was used to ensure the complete saturation of the vinyl groups in the polybutadiene block of the SES copolymer. The polydispersity index of the PS homopolymer was 1.06. The polydispersity indices of the PS and PB components of the SBS copolymer were both 1.02. The physical characterizations of PS and SES are described in TABLE 1.

TABLE 1

Physical characteristics of exemplary polymers used

| Polymer | PS M$_n$ (kg/mol) | PE M$_n$ (kg/mol) | PS Volume Fraction |
|---------|-------------------|-------------------|---------------------|
| PS      | 5.9               | —                 | 1                   |
| SES     | 13.8              | 37.4              | 0.41                |

Membrane Preparation

Certain embodiments of the present disclosure are directed to membranes and the preparation thereof. An exemplary protocol for preparing a membrane based on a sulfonated SES copolymer, according to one embodiment, is now described.

SES/PS blend solutions were prepared in o-xylene and gently stirred at 100° C. overnight. Solutions were then cast using doctor blade on ultraclean aluminum foil on a custom-built solvent caster heated to 80° C. The concentration of the solutions and the height of the doctor blade were adjusted to obtain membranes with a thickness ranging from 30 to 50 µm. The membranes were then dried under vacuum at 80° C. for 24 hours. After drying, the aluminum foil was removed by immersion in 1M hydrochloric acid. Resulting free-standing membranes were washed with deionized water several times and dried under vacuum overnight. The membranes were subsequently washed with THF (a selective solvent for PS) to remove the PS homopolymers and generate pores, and then immersed in methanol before a final drying in vacuum overnight. The weight of the membranes before and after selective dissolution of PS homopolymer was measured to ensure complete PS homopolymer removal. Pristine non-porous SES membranes were prepared following a similar procedure as above for an SES solution prepared without PS present.

Figure 3:
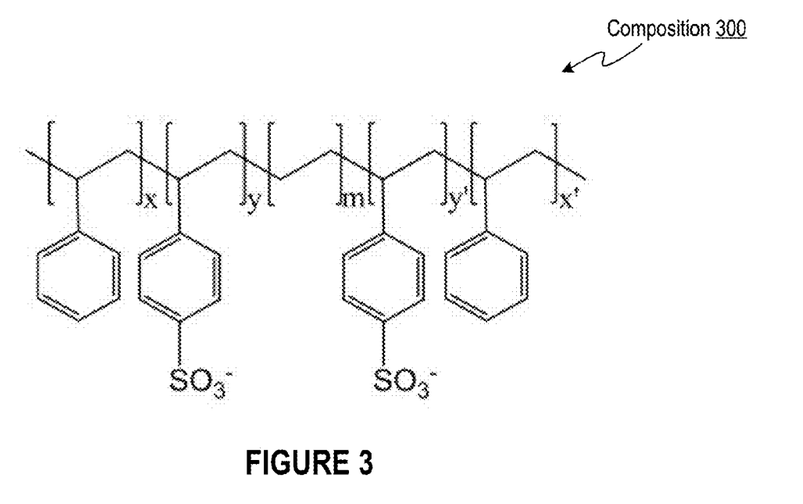
FIG. 3 illustrates a chemical composition of a membrane prepared in accordance with an embodiment of the disclosure.
Figure 4:
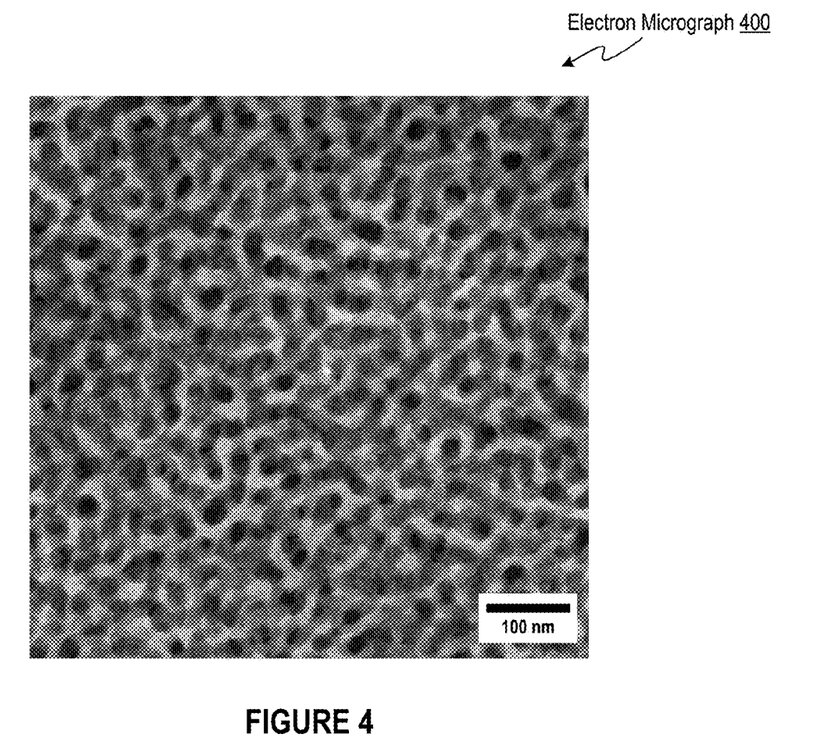
FIG. 4 is a micrograph showing the morphology of a membrane prepared in accordance with an embodiment of the disclosure.

Sulfonated-SES membranes, comprising poly(styrene sulfonate)-block-polyethylene-block-poly(styrene sulfonate) (PSS-PE-PSS) copolymer, were prepared as follows. SES membranes were sulfonated directly in a custom-designed three-neck reactor equipped with a porous polytetrafluoroethylene (PTFE) clamp. Specifically, a circular membrane with 2 inch diameter was punched out and held in place in the porous PTFE clamp inside the reactor. 90 mL of 1,2-dichloroethane was added to the reactor. The reactor was subsequently sealed and equipped with an addition funnel and a condenser. The mixture was heated to 40° C. and stirred under a dry N$_2$ environment for about an hour. Acetic sulfate was prepared by injecting 4.8 mL of acetic anhydride and 14.4 mL of dichloroethane into a sealed N$_2$-purged round-bottomed flask in an ice bath. The solution was allowed to cool to 0° C. before injecting 1.6 mL of 96% sulfuric acid into the flask. The mixture was immediately transferred to the reactor through the addition funnel. By adjusting the reaction time, the sulfonation level of the membranes was controlled to result in a sulfonation level of approximately 45%. The reaction was terminated with 20 mL of methanol, and the sulfonated membranes were subsequently washed with methanol several times and then soaked in deionized water for 5 days (which was replaced with fresh deionized water each day). The membranes were then maintained in deionized water prior to measurements. FIG. 3 illustrates a composition 300 of the sulfonated membrane. FIG. 4 is an electron micrograph 400 revealing the morphology of a 40% porosity membrane.

In Vitro Analysis of Membranes

For binding capacity and binding kinetics measurements, each membrane was fixed in place by a porous PTFE claim within a beaker containing a dox/PBS solution with a dox concentration of 0.05 mg/mL under constant stifling at 37° C. The solution also contained Ca$^{2+}$ and Mg$^{2+}$ to mimic blood electrolyte concentration. Binding kinetics was measured by drawing aliquots from the solution every 30 minutes for 24 hours. Dox concentration of the aliquots were measured using a UV-Vis absorption spectrometer and comparing to a standard calibration curve. Binding capacity was measured after the concentration of the dox solution was equilibrated. Each membrane had a fixed sulfonation level of 45%.

Figure 5A:
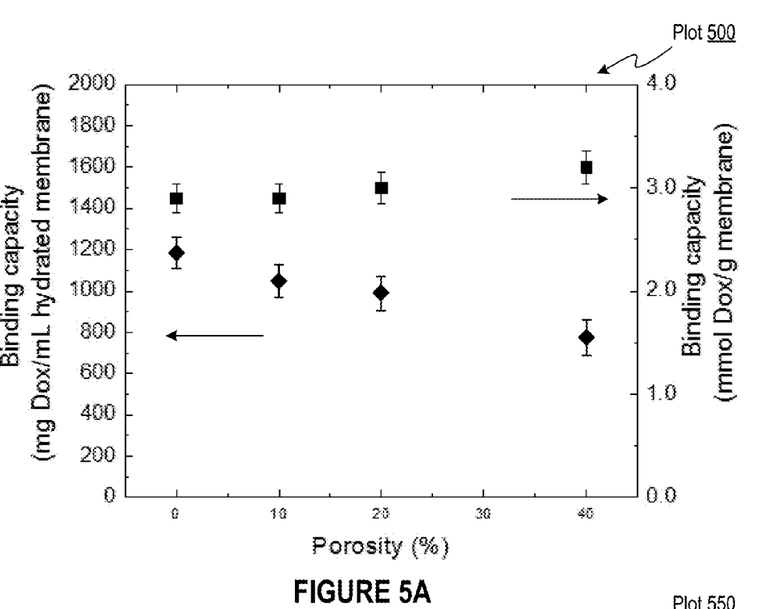
FIG. 5A is a plot showing doxorubicin binding capacity for membranes prepared in accordance with embodiments of the disclosure.

FIG. 5A is a plot 500 showing the binding capacity of membranes of varying porosity. All membranes demonstrated high binding capacity (data points denoted by squares) of about 3 mmol of dox per gram of dry membrane, with membranes of certain embodiments having a binding capacity of at least 2.5, at least 2.55, at least 2.6, at least 2.65, at least 2.75, at least 2.80, at least 2.85, at least 2.90, at least 2.95, at least 3.00, at least 3.05, at least 3.1, at least 3.15, at least 3.2, or at least 3.25 mmol of dox per gram of dry membrane for membranes having porosity (as defined above) of 0%, of at least 0%, or ranging from 0 to 40%. In an aqueous environment, such as an in vivo environment, membranes would absorb water and swell. The water uptake and swelling of the membranes increase with increasing porosity, leading to a slight decrease in the amount of bound dox (data points denoted by diamonds). Nevertheless, the dox binding capacity is unexpectedly greater than that of current materials, e.g., 5 times greater than the DOWEX™ resin and 20 times greater than drug eluting beads available from DC BEAD®. In certain embodiments, the binding capacity was at least 700 mg dox per mL hydrated membrane for membranes having porosity (as defined above) ranging from 0 to 40%. In certain embodiments, the binding capacity was at least 800 or at least 900 mg dox per mL hydrated membrane for membranes having porosity ranging from 0 to 20%. In certain embodiments, the binding capacity was at least 1000 mg dox per mL hydrated membrane for membranes having porosity ranging from 0 to 10%. In certain embodiments, the binding capacity was at least 1100 or at least 1200 mg dox per mL hydrated membrane for membranes having porosity less than 10%.

Figure 5B:
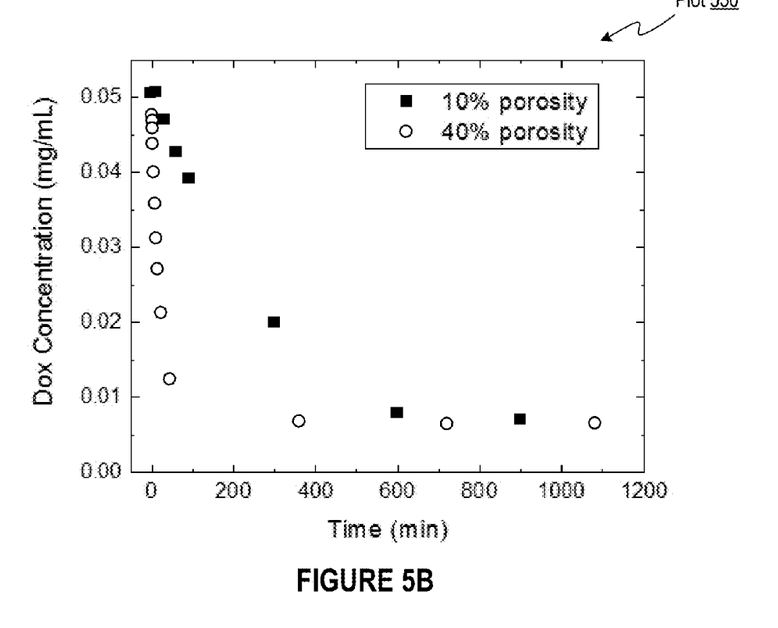
FIG. 5B is a plot showing doxorubicin binding kinetics for membranes prepared in accordance with embodiments of the disclosure.

FIG. 5B is a plot 550 showing the binding kinetics of membranes of varying porosity. In this experiment, membranes with 10% porosity and 40% porosity were compared. The membrane with 40% porosity bound about 35% of the drug in the first 10 minutes and over 80% in the first hour, which was significantly faster than membranes of lower porosities.

In Vitro Analysis of Ion-Exchange Resins

A closed-circuit flow model simulating intra-arterial chemotherapy (IAC) delivery was designed using an ion-exchange resin (DOWEX™, Sigma-Aldrich, St. Louis, Mo.). In order to test dox binding capacity and kinetics of the resin, the model was designed by employing a peristaltic pump (MASTERFLEX®, Vernon Hills, Ill.) with controlled flow rate to match human hepatic blood flow (approx. 750 mL; min). Polyvinyl chloride tubing also matched the average human hepatic vein, with the filter segment measuring 1.2 cm in diameter and 6 cm in length. A 1 L PBS buffer solution containing $Ca^{2+}$ and $Mg^{2+}$ was warmed to 37° C. in a glass vessel. The solution simulates physiologic serum electrolyte composition, pH, and temperature. Cations in the blood are theorized to be the primary competitors to dox binding, which is also cationic at body pH (7.4), however, the model accounts for this by matching serum electrolyte concentrations and molarity (0.150 M).

Within the flow-circuit, a filter column was introduced, filled with resin to a volume matching that of a cone in the hepatic vein (2.5 mL). The resin was immobilized in the circuit by a porous polyethersulfone dialysis mesh filter (GVS Filter Technology, Inc., Indianapolis, Ind.). The pore sizes ranged from 50 to 200 nm depending on resin particle size to allow for free passage of blood with acceptable pressure drops.

Various experiments were performed in the above-described flow model, including (1) a flow experiment, (2) an IAC experiment, (3) a serum experiment, and (4), a single pass experiment. Multiple samples were obtained over time (up to 90 min) from these experiments (or per pass for the single pass experiment), and dox concentrations were measured by UV spectrophotometry at a known wavelength of 480 nm. Dox concentrations (mg/mL) were plotted over time (or per pass for the single pass experiment). Control experiments were performed for each of the above experiments with the same parameters (as described below), but without resin in the system, to ensure that binding of dox to other components of the system, such as glass or tubing, was not significant. Statistical differences were explored using an unpaired Welch's t-test. All tests were one-sided and a converted P value of less than 0.05 was considered statistically significant. In the experiments, the t-test was conducted at each time point and analyzed compared to the control. The results indicate a 99.9% confidence interval for the flow experiments and IAC experiments, and a 95% confidence interval for the Serum experiment.

Figure 6A:
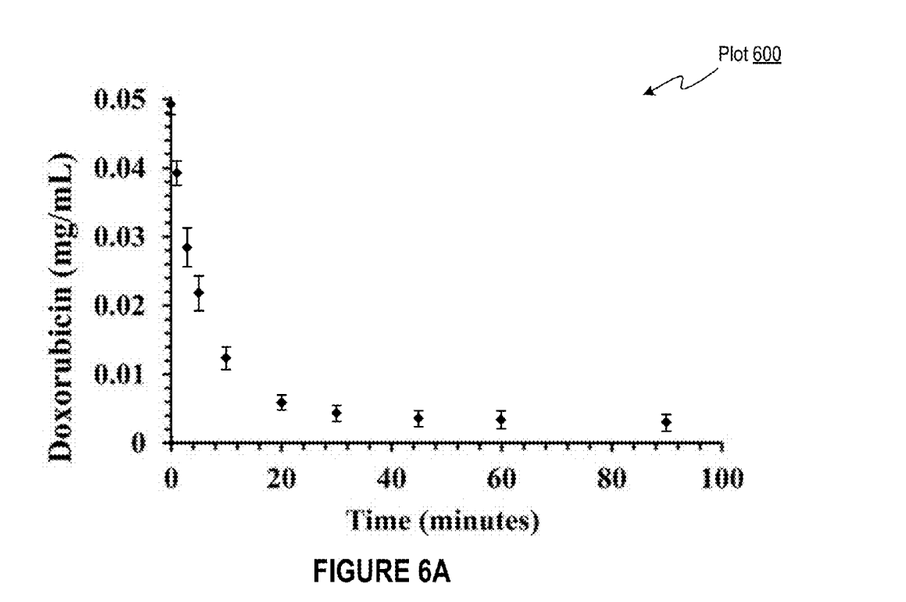
FIG. 6A is a plot showing dox clearance over time by a resin in a flow experiment.

Flow experiment: 50 mg of 2 mg/mL dox was introduced into the system in 1 L PBS and allowed to equilibrate over several minutes prior to circulating through the resin binding column. FIG. 6A is a plot 600 showing dox clearance over time for the flow experiment (with data presented as a mean±SD, n=6). The resin bound 76% (38 mg) of dox (50 mg) within the first 10 minutes, and 92% (46 mg) within the first 30 minutes (P<0.001), compared to control experiments with no resin where dox concentrations remained unchanged over time.

Figure 6B:
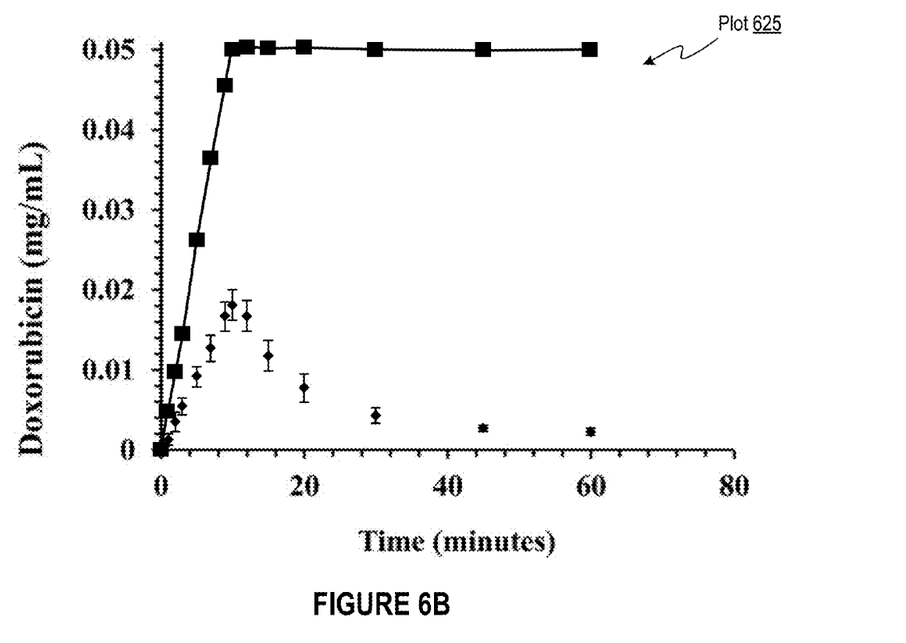
FIG. 6B is a plot showing dox clearance over time by a resin in a intra-arterial chemotherapy simulation experiment.

IAC experiment: 50 mg of dox (2 mg/mL) was infused slowly over 10 minutes (simulating clinical IAC) with resin filtration device. FIG. 6B is a plot 625 showing dox clearance over time for the IAC experiment (with data presented as a mean±SD, n=6). The resin filtered 64% (32 mg) of the injected dox (50 mg) within the first 10 minutes compared to controls. At 30 and 60 minutes, 92% (46 mg) and 96% (98 mg) of dox was cleared, respectively (P<0.001).

Figure 6C:
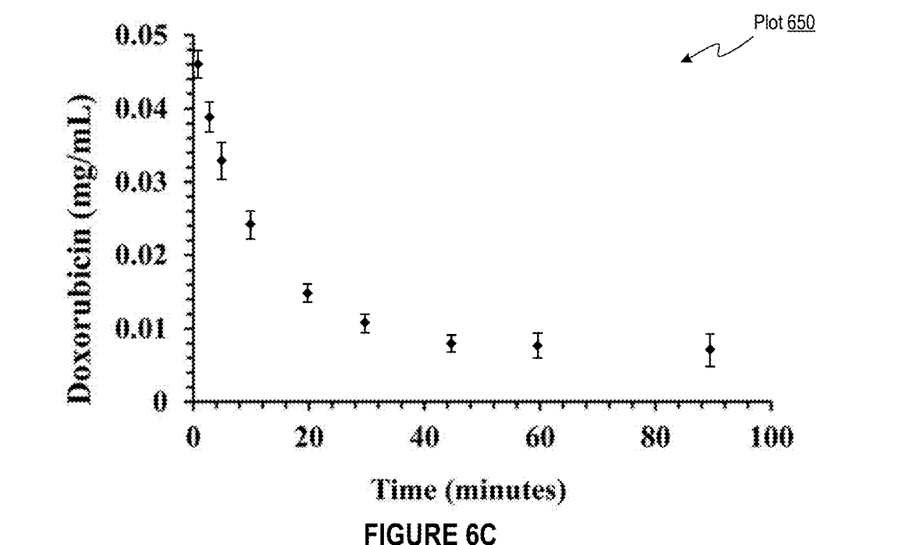
FIG. 6C is a plot showing dox clearance over time by a resin in a serum experiment.

Serum experiment: 50 mg of dox (2 mg/mL), was introduced into the system in 1 L of porcine serum and allowed to equilibrate over several minutes prior to contact with the resin. In this experiment, in order to test the binding capacity of resin in a complex physiologic solution, resin was added freely to the 1 L vessel containing the dox solution. FIG. 6C is a plot 650 showing dox clearance over time for the serum experiment (with data presented as a mean±SD, n=6). The results revealed slightly slower kinetics and binding capacity compared to binding from dox in PBS solution with approximately 52% (26 mg) of total dox mass bound (50 mg) after 10 minutes and 80% (40 mg) of total dox mass bound after 30 minutes (P<0.05).

Figure 6D:
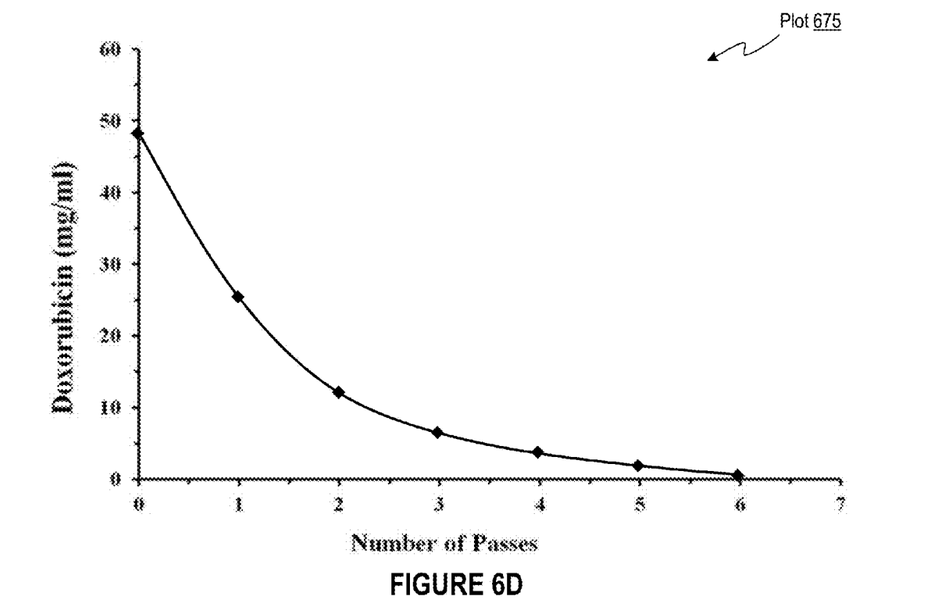
FIG. 6D is a plot showing dox clearance by a resin with increasing passes through the resin.

Single pass experiment: 50 mg of dox (2 mg/mL) was introduced into the system in 1 L PBS, and allowed to equilibrate over several minutes. The 1 L solution was passed through the resin binding column without any subsequent recirculation of the solution through the resin binding column. A sample was obtained of the subsequent solution. The solution was then passed through the same resin binding column again without any subsequent recirculation, and a sample was taken. This was performed several times to determine first pass effects of the resin without recirculation effects. FIG. 6D is a plot 675 showing dox clearance over time for the single pass experiment with increasing passes. A total of 6 passes were performed with starting dox concentration of 0.05 mg/mL, and final concentration of 0.0006 mg/mL. On average, dox concentration was reduced exponentially by 51% compared to each subsequent pass through the resin column. A total of 99% of the initial total drug mass was bound by the resin after 6 passes.

Chemofiltration Device Construction

Figure 7A:
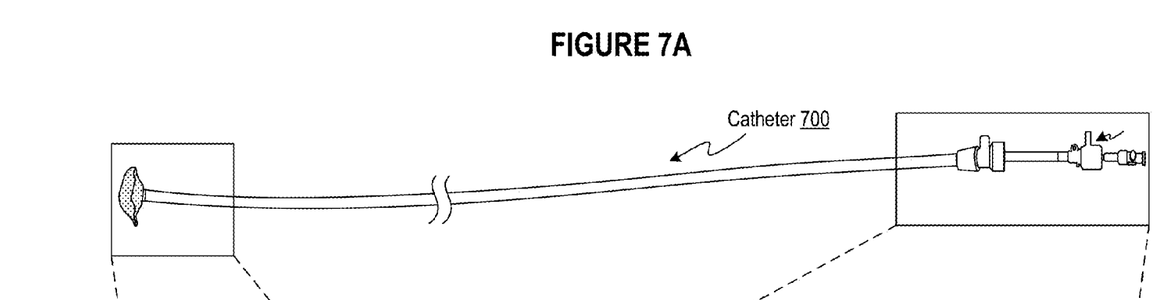
FIG. 7A is a photograph of a catheter incorporating a resin at its proximal end prepared in accordance with embodiments of the disclosure.
Figure 7B:
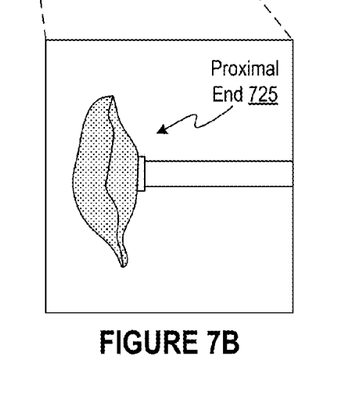
FIG. 7B is a photograph of a resin at a proximal end of a catheter prepared in accordance with embodiments of the disclosure.
Figure 7C:
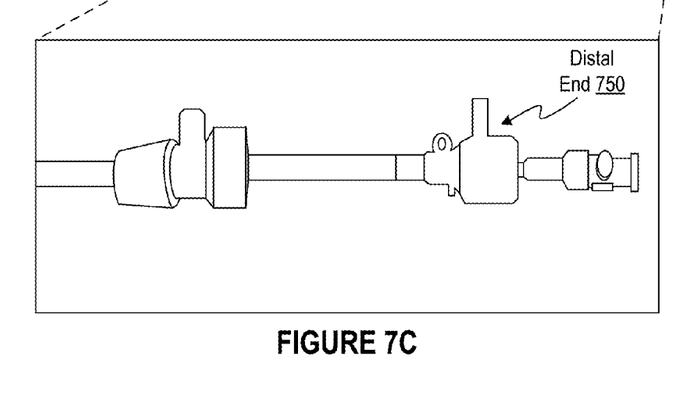
FIG. 7C is a photograph of a distal end of a catheter prepared in accordance with embodiments of the disclosure.

An 18 French (Fr) CF device (CF1) was constructed using resin, which included extruded plastic tubing for the catheter housing, stainless steel struts supporting a 200 micrometer nylon mesh dialysis membrane (GVS Filter Technology, Inc., Indianapolis, Ind.), which immobilized ion-exchange resin beads (approximately 250 micrometers in diameter) at the catheter tip. The device utilized an 18 Fr sheath (Cook Medical, Indianapolis, Ind.) in order to facilitate percutaneous delivery to the target via a jugular vein. Once deployed, the CF1 device 700 morphologically resembled a porous "tea-bag" containing resin beads at the proximal end 725 and a connector at the distal end 750, as shown in FIGS. 7A-7C. Blood can pass through and contact the resin material allowing dox to be ionically removed from the blood.

Figure 8:
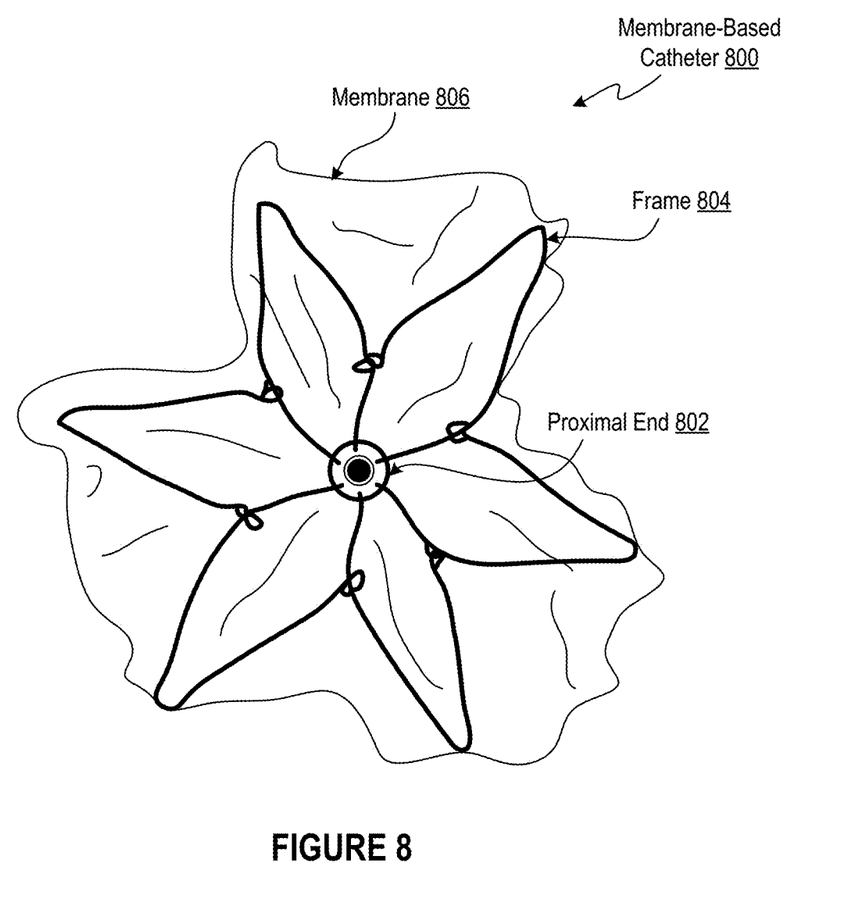
FIG. 8 is a photograph of a membrane affixed to a frame at a proximal end of a catheter prepared in accordance with embodiments of the disclosure.

A second 18 Fr CF device (CF2) was constructed with different geometry than the CF1 device. The CF2 device featured an expandable 28 mm diameter nitinol frame having a sulfonated copolymer membrane attached thereto, which covered part of the frame. The membrane was a 45±5 micrometer thick porous film PSS-PE-PSS triblock copolymer. The molecular weights of the PE and PSS (46% sulfonation) were 37 kg/mol and 19 kg/mol, respectively. The volume fraction of the pores was 40% and the average pore diameter was estimated to be 12 nanometers. The pores were lined by PSS chains. The center-to-center distance between adjacent pores was 51 nanometers when the membrane was hydrated. Deployment of the device is similar to that of the CF1 device. FIG. 8 illustrates the CF2 device, which shows a membrane-based device 800 in a deployed state. A membrane 806 is affixed to a frame 804 that extends from a proximal end 802 of a catheter.

Preclinical In Vivo Assessment

In vivo pilot experiments on swine were performed to establish an animal model and proof-of-concept for toxicity reduction. Farm swine (n=3, 30 kg) received humane care in compliance with the UCSF IACUC. Interventional procedures included anesthesia (Isoflurane), X-ray fluoroscopy, percutaneous transarterial catheterization of the hepatic artery, and percutaneous transveous catheterization of the vena cava. Heparin was not administered in order to prevent thrombus formation. Heart rate, electrocardiogram, and $O_2$-saturation were continuously monitored during the interventions. Animals were euthanized immediately after the procedures.

In the first animal, the CF1 filter was introduced percutaneously via the internal jugular vein (IJV) and deployed in the suprahepatic PVC. Insertion and deployment were assessed in this animal, and no chemotherapy was infused. Venograms were obtained during this procedure via contrast injection (Omnipaque) to assess patency of the venous system. Pressures were measured in the IVC via standard catheter techniques and a digital catheter pressure gauge. While blood flow was occluded, this was likely stasis due to impedance from the catheter tip containing densely packed resin, and not due to poor resin hemocompatibility. This was demonstrated by contrast venography performed 20 minutes after CF1 deployment, as well as IVC pressure measurements that revealed a significantly elevated pressure gradient of 20 to 30 mmHg (the baseline was 5 to 10 mmHg). Despite IVC occlusion, hemodynamic changes in the swine were minimal, likely due to collateral blood flow in the azygos system. The catheter was removed and the resin bag was examined ex vivo microscopically, revealing no evidence of thrombosis within the resin itself. This suggests that the occlusion was outside of the catheter and due to obstruction of flow by the resin-containing bag, rather than by the resin itself. Cation exchange resins contains highly sulfated groups that are similar to those found in heparin, aiding in biocompatibility and lowering thrombogenicity.

In the second animal, a CF device was not deployed, but rather a hepatic artery IAC infusion of dox was performed with subsequent sampling of blood at various times and positions throughout the venous system. This was performed in order to validate a hepatic dox IAC pharmacokinetic experimental model, measuring venous dox concentrations over time via a developed liquid chromatography-mass spectroscopy assay (Pacific Biolabs, Hercules, Calif.). In this animal, a microcatheter was advanced into the hepatic artery via standard access from a right femoral artery approach using fluoroscopy and contrast as needed. Via percutaneous UV access, central catheters were positioned with tips in the suprahepatic IVC and right hepatic vein. Next, 50 mg of dox (2 mg/mL) was adminis-tered into the liver via an infusion pump at a constant rate over 10 minutes. Blood samples were obtained for dox concentration measurements from each of the 3 above-described central and peripheral venous catheters, at times 0, 3, 10, 30, 60, and 90 minutes. There were no hemodynamic changes during the procedure.

Figure 9:
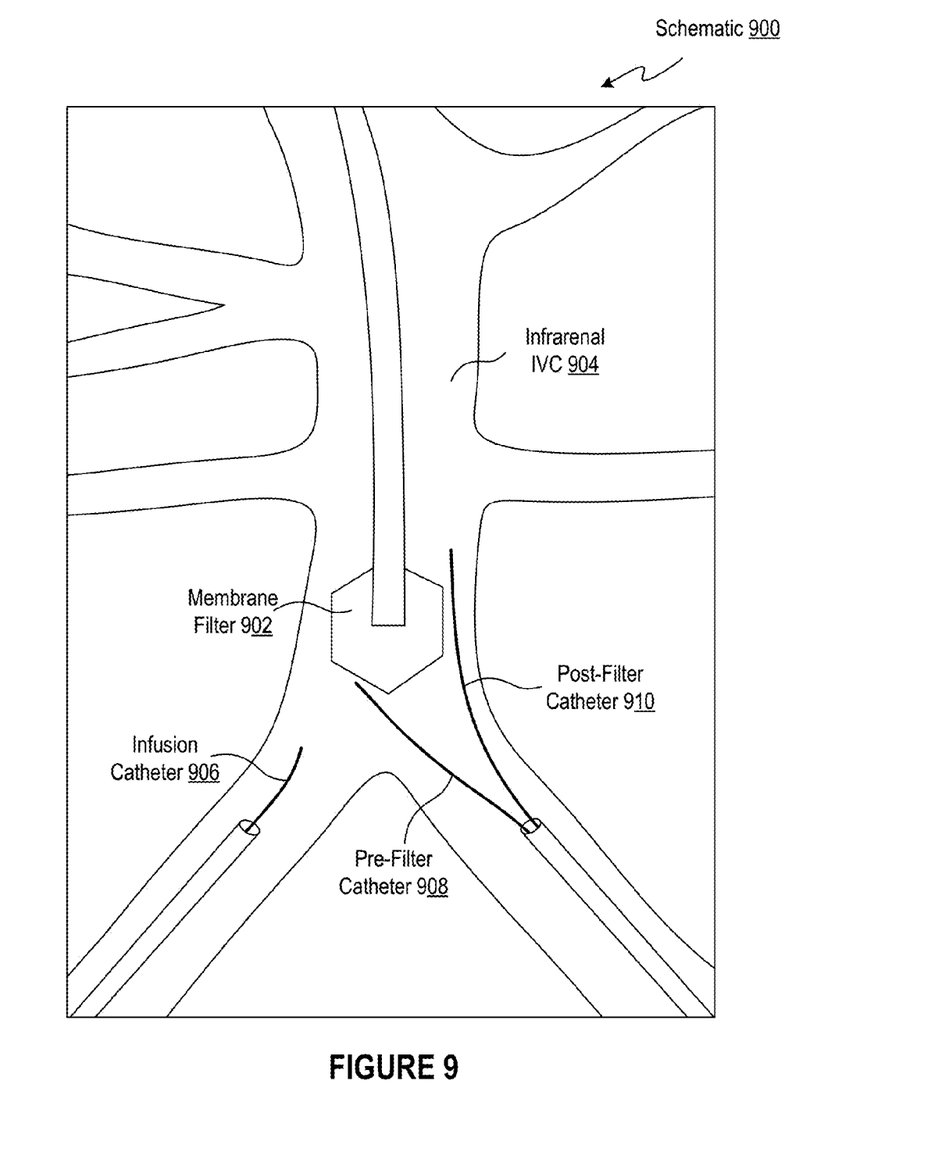
FIG. 9 illustrates an experimental setup using a membrane-based catheter prepared in accordance with embodiments of the disclosure.

In the third animal, under X-ray fluoroscopy and contrast venography, the CF2 device was percutaneously introduced via the internal jugular vein and deployed in the porcine infrarenal IVC. The experimental setup is illustrated by schematic 900 in FIG. 9, which shows a membrane filter 902 deployed within an infrarenal IVC 904. An infusion catheter 906 injects dox into the infrarenal IVC 904. In order to demonstrate binding in vivo solely from the blood, without effects from the liver, 50 mg of dox (2 mg/ml) was injected over 10 min in the IVC below the CF2 device. Venous catheters (pre-filter catheter 908 and post filter-catheter 910) with tips proximal and distal to the membrane filter 902 in the infrarenal IVC 904 obtained pressures and blood samples for dox concentrations over 90 minutes across the device. Pressure measurements taken throughout the experiment yielded a max gradient of 17 mmHg across the CF2 membrane. There were no hemodynamic instabilities based on vital signs. Venography demonstrated non-flow-limiting thrombus below the CF2 device after 90 min of deployment.

Figure 10:
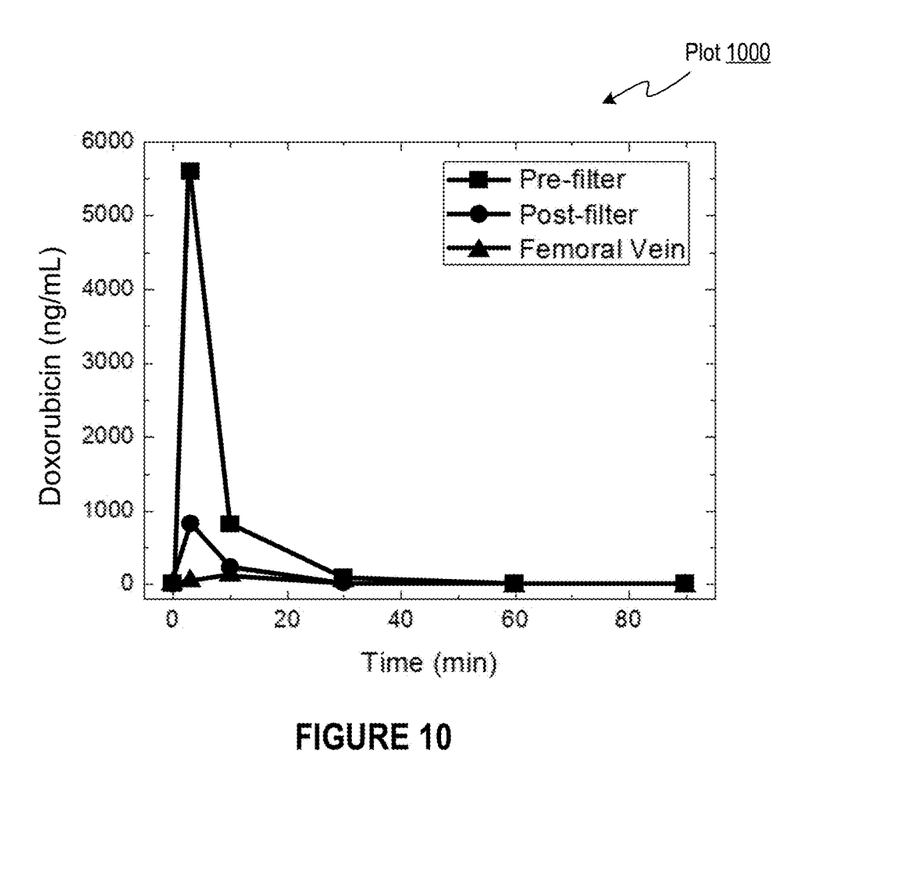
FIG. 10 is a plot showing doxorubicin concentrations at pre- and post-filter locations during an in vivo experiment.

FIG. 10 is a plot 1000 showing doxorubicin concentrations at pre- and post-filter locations during an in vivo experiment. Significant dox binding was observed with an 85%, 74%, and 83% decrease in relative pre-versus post-filter dox concentrations at times 3, 10, and 30 min, respectively, after the initiation of dox injection. The highest pre-filter doxorubicin level reached 5600 ng/mL, while the highest post-filter doxorubicin concentration was only around 800 ng/mL—almost a 7-fold decrease from the pre-filter concentration. By calculating the area under the curves we estimate the percentage of doxorubicin that was absorbed by the filter to be 81%, assuming constant flow rate.

In the foregoing description, numerous specific details are set forth, such as specific materials, dimensions, processes parameters, etc., to provide a thorough understanding of the present disclosure. The particular features, structures, materials, or characteristics may be combined in any suitable manner in one or more embodiments. For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments," or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The term "about", when referring to a physical quantity, is to be understood to include measurement errors within, and inclusive of 2%. For example, "about 100° C." should be understood to mean "100±1° C.".

It is to be understood that the above description is intended to be illustrative, and not restrictive. Many other embodiments will be apparent to those of skill in the art upon reading and understanding the above description. The specification and drawings are, accordingly, to be regarded in an illustrative rather than a restrictive sense. The scope of the disclosure should, therefore, be determined with reference to the appended claims, along with the full scope of equivalents to which such claims are entitled. Various modifications of the disclosed embodiments in addition to those shown and described herein will become apparent to those skilled in the art and are intended to fall within the scope of the appended claims.

What is claimed is:

1. A porous membrane comprising poly(styrenesulfonate)-block-polyethylene-block-poly(styrenesulfonate), the membrane having an average pore volume fraction of less than 40% and a sulfonation level of about 45%;
    wherein the pores are lined by poly(styrenesulfonate) chains; and
    wherein a doxorubicin binding capacity of the membrane is about 3 mmol doxorubicin per gram of dry weight of the membrane.

2. The membrane of claim 1, wherein the thickness of the membrane ranges from 30 µm to 50 µm.

3. The membrane of claim 1, wherein a 2 inch diameter sample of the membrane, when immersed in an aqueous solution containing 50 mg of doxorubicin at a concentration of 0.05 mg/mL at 37° C., is to absorb about 35% of the doxorubicin from the solution within 10 minutes of immersion.

4. The membrane of claim 1, wherein the membrane is incorporated into a catheter.

5. A catheter comprising:
    a tubular housing;
    a frame disposed at a proximal end of the tubular housing, wherein the frame is expandable to switch between a collapsed state and a deployed state; and
    a porous membrane affixed to the frame, the membrane comprising a poly(styrene sulfonate)-block-polyethylene-block-poly(styrenesulfonate), the membrane having an average pore volume fraction of less than 40% and a sulfonation level of about 45%;
    wherein the pores are lined by poly(styrenesulfonate) chains; and
    wherein a doxorubicin binding capacity of the membrane is about 3 mmol doxorubicin per gram of dry weight of the membrane.

6. The catheter of claim 5, wherein the membrane is contained within the housing when the frame is in the collapsed state, and wherein the membrane is outside of the housing and extends radially from the proximal end when the frame is in the deployed state.

7. The catheter of claim 5, wherein the frame comprises nitinol.

* * * * *